United States Patent [19]

Meier

[11] 3,988,459
[45] Oct. 26, 1976

[54] NOVEL ANALGESIC COMPOSITIONS
[75] Inventor: Jean Meier, La Varenne Saint-Hilaire, France
[73] Assignee: Roussel-UCLAF, Paris, France
[22] Filed: May 6, 1975
[21] Appl. No.: 575,023

[30] Foreign Application Priority Data
May 9, 1974 France .............................. 74.16018

[52] U.S. Cl. ................................. 424/258; 424/316
[51] Int. Cl.² ................ A61K 31/47; A61K 31/205
[58] Field of Search ............................ 424/316, 258

*Primary Examiner*—Stanley J. Friedman
*Attorney, Agent, or Firm*—Hammond & Littell

[57] ABSTRACT

Novel analgesic compositions comprising an effective amount of (A) a member of the group consisting of 4-[o-(2',3'-dihydroxypropyloxycarbonyl)-phenyl]-amino-8-trifluoromethyl-quinoline and its non-toxic, pharmaceutically acceptable acid addition salts and (B) a compatible therapeutically effective salt of a strong acid and a weak base having a superior analgesic activity.

11 Claims, No Drawings

NOVEL ANALGESIC COMPOSITIONS

OBJECTS OF THE INVENTION

It is an object of the invention to provide novel superior analgesic compositions.

It is a further object of the invention to provide a novel method of relieving pain in warm-blooded animals.

These and other objects and advantages of the invention will become obvious from the following detailed description.

THE INVENTION

The novel analgesic compositions of the invention are comprised of (A) a member of the group consisting of 4-[o-(2',3'-dihydroxypropyloxycarbonyl)-phenyl]-amino-8-trifluoromethyl-quinoline and its non-toxic, pharmaceutically acceptable acid addition salts and (B) a compatible therapeutically effective salt of a strong acid and a weak base. The said quinoline is preferably used in the form of an acid addition salt with a strong acid.

Examples of suitable non-toxic, pharmaceutically acceptable strong acids are inorganic acids such as hydrochloric acid, hydrobromic acid, sulfuric acid and phosphoric acid and organic acids such as maleic acid, α-ketoglutaric acid and sulfonic acids such as methane sulfonic acid and p-toluenesulfonic acid.

In a preferred composition of the invention, compound A is the hydrochloride salt of 4-[o-(2',3'-dihydroxypropyloxycarbonyl)-phenyl]-amino-8-trifluoromethyl-quinoline and compound B is the hydrochloride salt of an amino acid or amino acid derivative such as betaine or lysine. The preferred weak base is betaine.

The most preferred composition of the invention is comprised of 1 part by weight of 4-[o-(2',3'-dihydroxypropyloxycarbonyl)-phenyl]-amino-8-trifluoromethyl-quinoline hydrochloride and 0.5 to 2.5 parts by weight of betaine hydrochloride and optionally a pharmaceutical carrier.

The analgesic properties of 4-[o-(2',3'-dihydroxypropyloxycarbonyl)-phenyl]-amino-8-trifluoromethyl-quinoline and its non-toxic, pharmaceutically acceptable acid addition salts are known and have been prepared in Belgium Pat. No. 725,641. The analgesic properties of diverse weak bases have never been described. It is therefore surprising that the compositions of the invention have a greater analgesic activity than an equal amount of the corresponding quinoline alone.

The analgesic compositions of the invention are useful for the treatment of muscular, articular or nervous pains, of toothaches, of migraines, of rhumatismic affections, of lumbagos, of zonas and as a complementary treatment for infectious or feverish states. The compositions may be in various forms such as gelules or drinkable solutions or emulsions.

The novel method of the invention for relieving pain in warm-blooded animals comprising administering to warm-blooded animals an analgesically effective amount of a composition comprising (A) a member of the group consisting of 4-[o-(2',3'-dihydroxypropyloxycarbonyl)-phenyl]-amino-8-tri-fluoromethyl-quinoline and its non-toxic, pharmaceutically acceptable acid addition salts and (B) a compatible therapeutically effective salt of a strong acid and a weak base. The products are preferably administered orally and at a daily dose of 4 to 20 mg/kg.

In the following examples there is described a preferred embodiment to illustrate the invention. However, it is to be understood that the invention is not intended to be limited to the specific embodiment.

EXAMPLE 1

An analgesic test based on the procedure of Koster et al (Fed. Prod., Vol. 18 (1959), p. 412) was used with 4-[o-(2',3'-dihydroxypropyloxycarbonyl)-phenyl]-amino-8-trifluoromethyl-quinoline hydrochloride (product A) and the same amount of the said quinoline plus 50 percent by weight of betaine hydrochloride as product B. The test was effected on mice who received an intraperitoneal injection of acetic acid which provoked repeated movements characterized by stretching and twistings that can persist for more than 6 hours. Analgesics prevent or suppress those syndromes which are considered to be exteriorisation of diffuse abdominal pains. The solution was 6% acetic acid in water containing 10% of arabic gum and the dose releasing the syndromes under these conditions was 0.01 ml/g or 60 mg/kg of acetic acid. The test products were administered one half hour before the intraperitoneal injection of acetic acid. The mice were not fed from the day before the test and groups of 5 mice were used for each dose and for the controls. Immediately after the acetic acid injection, the number of stretching for each animals was counted for 15 minutes and the tests were repeated three times. The results are in Table I.

TABLE I

| Doses in mg/kg* | Number of animals | Average Number of stretching per mouse | % of protection |
|---|---|---|---|
| Product A | | | |
| 0 | 15 | 77 ± 6 | |
| 5 | 15 | 54 ± 7 | 30 |
| 10 | 15 | 39 ± 4 | 50 |
| 20 | 15 | 9 ± 2 | 89 |
| Product B | | | |
| 10 | 15 | 27 ± 4 | 65 |
| 20 | 15 | 24 ± 3 | 69 |
| 40 | 15 | 9 ± 2 | 89 |

*expressed in mg of free base.

From the data of Table I, the $DA_{50}$ dose or the dose which reduces the number of stretchings by 50% is 8.5 mg/kg for product A and 6.0 mg/kg for product B. This means that product B has about 25% greater analgesic activity than product A.

The acute toxicity was determined from products A and B on Sprague Dawley male rats weighing between 110 and 120 g and the products were orally administered with an esophagous probe. The $DL_{50}$ dose or the dose at which 50% of the animals died was 850 mg/kg for product A and 790 mg/kg for product B which means the two products have comparable toxicities.

EXAMPLE 2

Gelules were prepared from 230 mg of 4-[o-(2',3'-dihydroxypropyloxycarbonyl)-phenyl]-amino-8-trifluoromethyl-quinoline hydrochloride, 200 mg of betaine hydrochloride, 10 mg of polyvinylpyrrolidone and 5 mg of Aerosil (colloidal silica) in water.

Various modifications of the compositions and method of the invention may be made without departing from the spirit or scope thereof and it should be understood that the invention is to be limited only as defined in the appended claims.

I claim:
1. An oral analgesic composition comprising an effective amount of (A) 1 part by weight of a member of the group consisting of 4-[o-(2',3'-dihydroxypropyloxycarbonyl)-phenyl]-amino-8-trifluoro-methyl-quinoline and its non-toxic, pharmaceutically acceptable acid addition salts and (B) 0.5 to 2.5 parts by weight of a compatible therapeutically effective salt of a strong acid and a member selected from the group consisting of amino acids and their betaines.
2. The composition of claim 1 wherein the said quinoline is in the form of a salt with a strong acid.
3. The composition of claim 2 wherein the strong acid is hydrochloric acid.
4. The composition of claim 1 wherein acid salt of the weak base is the hydrochloride.
5. The composition of claim 1 wherein the weak base is an amino acid compound.
6. The composition of claim 5 wherein weak base is betaine.
7. An oral analgesic composition comprising 1 part by weight of 4-[o-(2',3'-dihydroxypropyloxycarbonyl)-phenyl]-amino-8-trifluoromethyl-quinoline hydrochloride and 0.5 to 2.5 parts by weight of betaine hydrochloride and optionally a pharmaceutical carrier.
8. A method of relieving pain in warm-blooded animals orally administering to warm-blooded animals an analgesically effective amount of a composition of claim 1.
9. The method of claim 8 wherein the quinoline is in the form of its hydrochloride salt.
10. The method of claim 8 wherein the salt of the weak base and the strong acid is the hydrochloride of an amino acid compound.
11. The method of claim 8 wherein the compatible salt is betaine hydrochloride.

* * * * *